US011338069B2

(12) United States Patent
Yang et al.

(10) Patent No.: US 11,338,069 B2
(45) Date of Patent: May 24, 2022

(54) FLUORESCENT AND/OR NIR COATINGS FOR MEDICAL OBJECTS, OBJECT RECOVERY SYSTEMS AND METHODS

(71) Applicant: The Regents of the University of California, Oakland, CA (US)

(72) Inventors: Jian Yang, San Diego, CA (US); James Wang, San Diego, CA (US); Christopher Barback, San Diego, CA (US); Erin Ward, La Jolla, CA (US); Natalie Mendez, La Jolla, CA (US); Sarah Blair, San Diego, CA (US); Andrew C. Kummel, San Diego, CA (US); William C. Trogler, Del Mar, CA (US); Tsai W. Sung, La Jolla, CA (US)

(73) Assignee: The Regents of the Unversity of California, Oakland, CA (US)

( * ) Notice: Subject to any disclaimer, the term of this patent is extended or adjusted under 35 U.S.C. 154(b) by 526 days.

(21) Appl. No.: 16/080,247

(22) PCT Filed: Feb. 28, 2017

(86) PCT No.: PCT/US2017/019975
§ 371 (c)(1),
(2) Date: Aug. 27, 2018

(87) PCT Pub. No.: WO2017/151634
PCT Pub. Date: Sep. 8, 2017

(65) Prior Publication Data
US 2019/0381218 A1 Dec. 19, 2019

Related U.S. Application Data

(60) Provisional application No. 62/301,312, filed on Feb. 29, 2016.

(51) Int. Cl.
| A61L 31/10 | (2006.01) |
| A61B 1/06 | (2006.01) |
| A61B 1/07 | (2006.01) |
| A61B 1/313 | (2006.01) |
| A61B 5/00 | (2006.01) |
| A61L 31/14 | (2006.01) |
| C09K 11/08 | (2006.01) |
| C09K 11/06 | (2006.01) |
| C09K 11/62 | (2006.01) |

(52) U.S. Cl.
CPC ............ *A61L 31/10* (2013.01); *A61B 1/0638* (2013.01); *A61B 1/07* (2013.01); *A61B 1/3132* (2013.01); *A61B 5/0071* (2013.01); *A61L 31/14* (2013.01); *C09K 11/06* (2013.01); *C09K 11/08* (2013.01); *C09K 11/0811* (2013.01); *C09K 11/0883* (2013.01); *C09K 11/62* (2013.01); *A61L 2300/442* (2013.01); *A61L 2420/02* (2013.01); *A61L 2420/06* (2013.01)

(58) Field of Classification Search
CPC ......... C09K 11/06; C09K 11/08; C09K 11/02; C09K 11/0811; C09K 11/565; C09K 11/0883; C09K 2211/1088; C09K 2211/1037; C09K 2211/1011; A61F 2250/0079
See application file for complete search history.

(56) References Cited

U.S. PATENT DOCUMENTS

| 4,114,601 A | 9/1978 | Abels |
| 5,190,059 A | 3/1993 | Fabian et al. |
| 5,816,238 A | 10/1998 | Burns et al. |
| 8,956,682 B2 | 2/2015 | Lockwood et al. |
| 2008/0095816 A1 | 4/2008 | Gordy et al. |
| 2012/0082713 A1 | 4/2012 | Meyering et al. |
| 2013/0108552 A1 | 5/2013 | Sharma et al. |
| 2015/0182673 A1 | 7/2015 | Delaney, Jr. et al. |
| 2015/0266290 A1 | 9/2015 | Dooley et al. |
| 2015/0284627 A1 | 10/2015 | Bohmer et al. |
| 2015/0368553 A1 | 12/2015 | Nelson et al. |

FOREIGN PATENT DOCUMENTS

| WO | 2007126411 A3 | 11/2007 |
| WO | 2016012350 A1 | 1/2016 |
| WO | WO 2016/077259 | * 5/2016 |

OTHER PUBLICATIONS

Shane Thomas, International Search Report for Application No. PCT/US2017/019975, dated May 19, 2017.
Cima et al., "Using a data-matrix-coded sponge counting system across a surgical practice: impact after 18 months," Joint Commission journal on quality and patient safety, vol. 37, pp. 51-58, 2011.
Egorova et al., "Managing the prevention of retained surgical instruments: what is the value of counting?" Ann Surg., vol. 247, pp. 13-18, 2008.
Fencl, Guideline Implementation: Prevention of Retained Surgical Items, AORN J., vol. 104, pp. 37-48, 2016.
Gibbs, "Retained Surgical Items and Minimally Invasive Surgery", World J. Surg., vol. 35, pp. 1532-1539, 2011.
Greenberg et al., "Bar-coding surgical sponges to improve safety: a randomized controlled trial," Ann Surg., vol. 247, pp. 612-616, 2008.
Jackson et al., "Counting Difficulties: Retained Instruments, Sponges, and Needles," AORN Journal, vol. 87, No. 2, pp. 315-321, 2008.

(Continued)

*Primary Examiner* — C Melissa Koslow
(74) *Attorney, Agent, or Firm* — Greer, Burns & Crain, Ltd.; Steven P. Fallon (57) ABSTRACT

A composition for coating a medical device and a coated medical device are provided. The composition includes a polymeric matrix having non-toxic quantum dots or a fluorophore or both. The polymeric matrix contains the quantum dots or fluorophore and binds as a coating to the medical device. Coated medical devices can be readily identified within or outside of a body and in open or laparoscopically surgeries, greatly reducing or eliminating the risk of a retained foreign object.

18 Claims, 2 Drawing Sheets

(56) References Cited

OTHER PUBLICATIONS

Lincourt et al., "Retained foreign bodies after surgery," J Surg Res., vol. 138, pp. 170-174, 2007.
Macilquham et al, "Identifying lost surgical needles using radiographic techniques," AORN J., vol. 78, pp. 73-78, 2003.
Soyer et al., "Retained surgical needle after laparoscopic sacrocolporectopexy: usefulness of CT fluoroscopy-guided hook-wire placement before surgical removal," Clinical Radiology, vol. 63, pp. 688-690, 2008.
Wan et al., "Improving safety in the operating room: a systematic literature review of retained surgical sponges," Current Opinion in Anesthesiology, vol. 22, No. 2, pp. 207-214, 2009.
Yang et al., "Ultrasound Responsive Macrophase-Segregated Microcomposite Films for in Vivo Biosensing", ACS Appl. Mater. Interfaces, vol. 9, No. 2, pp. 1719-1727, 2017.

* cited by examiner

FLUORESCENT AND/OR NIR COATINGS FOR MEDICAL OBJECTS, OBJECT RECOVERY SYSTEMS AND METHODS

PRIORITY CLAIM AND REFERENCE TO RELATED APPLICATION

The application claims priority under 35 U.S.C. § 119 and all applicable statutes and treaties from prior U.S. provisional application Ser. No. 62/301,312, which was filed Feb. 29, 2016.

FIELD

A field of the invention is medical devices, including implants and surgical devices. Another field of the invention is surgical systems and surgical methods.

BACKGROUND

Surgical retained foreign objects have significant potential negative consequences for patients, doctors and hospitals. See, e.g. Lincourt et al., "Retained foreign bodies after surgery," J Surg Res. 138:170-4 (2007). Clinical consequences for retained foreign objects can range from sepsis, to wound infections, to even death in rare circumstances. A majority of patients with a retained foreign object, estimated between 69-83%, require additional surgical interventions to remove the object. Lost smaller items such as needles are particularly challenging. Retained foreign objects such as surgical needles, vessel loops and blades accidentally left in patients' bodies in operating rooms, occur in 12.5% of surgeries and can cause serious consequences to the patient. Consequences to the patient such as organ damage, bowel perforation, severe pain, sepsis, and even death. Jackson, S., et al., "Counting Difficulties: Retained Instruments, Sponges, and Needles," A ORN Journal, 87 (2), 315-3212, (2008). The serious health problems caused to patients from retained foreign objects can lead to significant financial problems for doctors and hospitals as the result of malpractice suits and judgements.

Surgical object counting, manually and with aides such as bar codes, remains the most commonly used method for retained foreign object prevention. Fencl J L., "Guideline Implementation: Prevention of Retained Surgical Items, AORN J. 104:37-48 (2016); Wan, W., et al., "Improving safety in the operating room: a systematic literature review of retained surgical sponges," Current Opinion in Anesthesiology, 22(2), 207-214, (2009); Greenberg C C et al. "Bar-coding surgical sponges to improve safety: a randomized controlled trial," Ann Surg. 247:612-6 (2008). However, a counting discrepancy could imply that a medical device is left in the patient's body, the operation table or cloth, or the operation room floor. The counting methods are far from ideal, however, as miscounts occur and accurate counts that show a missing object do not demonstrate that the object is in the patient, because the object can be elsewhere in the surgical field. When a count cannot be remedied, which can be as often as 1 in 8 surgeries, protocols dictate that the surgery be paused and that all participating personnel search for the object in and around the surgical field including within the body. See, Fencl, J L., supra.

Miscounts that are not remedied lead to additional patient X-rays, which are commonly used as a back-up for counting methods. Another approach involves positive detection of medical devices to locate RSI inside or outside the body cavity. While X-rays are commonly used as a backup for counting errors, studies show that X-ray images are neither particularly specific nor sensitive intraoperatively, and they are particularly poor for location of needles. Egorova N N, et al. "Managing the prevention of retained surgical instruments: what is the value of counting?" Ann Surg. 247:13-8 (2008); Macilquham M D, et al, "Identifying lost surgical needles using radiographic techniques," AORN J. 78:73-8 (2003).

X-ray imaging in the operating room is especially poor, and the poor imaging quality can fail to discover a retained foreign object in the body. Macilquham et al. studied X-ray imaging to identify lost surgical needles and found that needles less than 20 mm were difficult to identify by surgeons. Macilquham M D, et al, supra. The X-ray imaging also poses an unnecessary radiation exposure hazard. to the patient and medical personnel.

Radiofrequency (RF) labeling has also been used for RSI detection and prevention. By utilizing RF transmission chip labels, surgical equipment used in surgeries can be detected by a RF detection mat or wand. Cima R R, et al. "Using a data-matrix-coded sponge counting system across a surgical practice: impact after 18 months," Joint Commission journal on quality and patient safety, 37:51-8 (2011); Fabian et al., U.S. Pat. No. 5,190,059, Surgical Implement Detector Utilizing a Powered Marker; Abels U.S. Pat. No. 4,114,601. Active device methods are practical for large surgical implements, such as sponges, but are not particularly useful for smaller items due to the size of the transmitter chip. The chip cannot be attached to small surgical tools, such as needles and blades.

Apart from such needles, other medical objects can be lost during surgical procedures, or can be inserted at other than a desired location. Medical devices such as medical implants, image guided injection needles, and biopsy markers must be located during various surgical procedures. Even though small incisions are made and few surgical items are used, minimally invasive surgery (MIS) cases are not immune to the problem of inadvertent surgical item retention. Sponges and needles left in patients' bodies during laparoscopic surgery are also an issue of concern. Gibbs, V., "Retained surgical items and minimally invasive surgery," World Journal of surgery. 35, 1532-1539 (2011); Soyer, P, Valleur, P., "Retained surgical needle after laparoscopic sacrocolporectopexy: usefulness of CT fluoroscopy-guided hook-wire placement before surgical removal," Clinical Radiology, 63, 688-690 (2008).

SUMMARY OF THE INVENTION

A preferred composition for coating a medical device is a polymeric matrix including non-toxic quantum dots or a fluorophore, such as a fluorescent dye, wherein the polymeric matrix contains the quantum dots or fluorophore and binds as a coating to the medical device. Coated medical devices can be readily identified within or outside of a body and in open or laparoscopical surgeries, greatly reducing or eliminating the risk of a retained foreign object. In preferred embodiments, the polymeric matrix is selected from the group consisting of epoxy adhesive, cyanoacrylate glue, polymeric organosilicone, and polymeric gels. In preferred embodiments, the quantum dots are selected from the group consisting of III-V group compounds, I-III-VI$_2$ group compounds, and ZnS/ZnSe nanocrystals. In preferred embodiments, the fluorophore is selected from the group consisting of inorganic fluorescent dyes, organic fluorescent dyes, and luminescent metal doped alumina, rubrene, rhodamine, indocyanine green, and dansyl chloride. The medical device

DETAILED DESCRIPTION OF THE PREFERRED EMBODIMENTS

The invention provides methods to coat, coating compositions, fluorescent and/or NIR (near infrared) coatings for medical devices and medical devices with fluorescent and/or NIR coatings. The invention also relates to surgical systems including medical devices with coatings and instruments to stimulate a visible response from the medical devices to aid surgeons during a procedure in locating the medical devices. A particular application of preferred coating compositions is to surgical instruments, such as surgical needles, forceps and razor blades. Other applications include medical implants, image guided injection needles, and biopsy markers. Coatings of the invention can help a person to locate lost medical devices, can also be used to monitor medical implants over time, and can be used to mark tissues and organs for other applications, such as small tumors for surgery.

To the knowledge of the present inventors, there is no viable universal platform for detecting retained foreign objects of different sizes and materials real-time during a surgical operation. Preferred embodiment methods for coating, coating compositions, fluorescent and/or NIR coatings and coated medical devices provide practical solutions for detecting retained foreign objects of different sizes and materials in real-time during surgical procedures.

Preferred coating methods deposit microscale fluorescent and/or NIR coatings on medical devices for effective in vivo and in vitro detection. A preferred fluorescent and/or NIR coating is a polymer film, with thickness approximately between 5 μm and 20 μm, containing fluorescent and/or NIR quantum dots or fluorophores and which can be deposited on various materials such as metal, plastic or glass. Preferred fluorescent and/or NIR film coated medical devices emit strong fluorescence in the visible or near infrared (NIR) light range and can be located using human vision or a NIR detector with simple black light (UV) illumination or with a NIR excitation source in detection methods of the invention. Preferred embodiments of the invention include fluorescent and/or NIR coated surgical equipment, such as fluorescent and/or NIR coated surgical needles, forceps and razor blades. Additional preferred embodiments include fluorescent and/or NIR coated medical implants, such as fluorescent and/or NIR coated image guided injection needles, and biopsy markers.

A preferred composition and coating for a medical device is a biocompatible polymeric matrix decorated with non-toxic quantum dots or fluorescent and/or NIR dyes. The polymeric matrix provides a scaffold for the fluorescent and/or NIR materials. Polymers used as matrix can be polymeric adhesives such as epoxy adhesive, cyanoacrylate glue or polymeric organosilicones; the polymer can also be polymeric gels, such as hydrogels or organogels. The polymeric matrix holds the quantum dots or fluorophore, such as a fluorescent dye and/or an NIR dye to form a thin film, which allows coating with a thickness ranging from 5 μm to 20 μm (micrometers) in preferred embodiments. The thin film can be coated on the surface of metal, plastic or glass, indicating that many medical devices can be coated. The matrix can also be fabricated in a 3D formulation with flexible shape and volume and other thicknesses. Preferred non-toxic quantum dots include the III-V group compounds (e.g., InP), I-III-VI2 group (e.g., CuInS2) and ZnS or ZnSe nanocrystals of low toxicity. Preferred fluorophores include inorganic or organic dyes, luminescent metal doped alumina, rubrene, rhodamine, indocyanine green, and dansyl chloride.

Additional materials may include upconverting materials that may contain two rare earth metal ions. One of the ions can be excited in the near infrared spectral region. A diode laser or LED can be used to stimulate fluorescence.

In a preferred search method, a medical device with a coating of the invention including a matrix containing fluorescent and/or NIR materials is stimulated by a low-power ultraviolet light ("black light") source with an excitation wavelength between 320 nm to 400 nm, which is safe for in vivo usage. The fluorescence emission of the quantum dots or fluorophore lies within the visible light range and can be easily visualized with different color choices from blue to red colors. For NIR emitting quantum dots or fluorescent dyes, an NIR source, such as a diode laser can be used as the excitation light source and a NIR detector can be used to locate the coated items. Quantum dots are highly photostable and have a high quantum yields as fluorescent and/or NIR markers. The fluorescence of quantum dots cannot be quenched by bioactive molecules in blood and tissues. The polymeric film can combine with the surface of surgical equipment, artificial tissues and other implants made with metal, plastic or glass. The detection of 2D and 3D fluorescent and/or NIR markers can be carried out during surgery with a portable black light without the need to rearrange the patient on the surgical table as required for other imaging modalities, such as X-ray computerized tomography (CT) or magnetic resonance imaging (MRI).

Preferred methods for coating and coatings of the invention can be used to coated surgical needles of any size. Example experiments demonstrated coatings on needles as small as 10 mm Under black light, the coated devices exhibit fluorescence when on the surface of organs in the patient's body, as well as the operation table, and floor. NIR emitting materials coated on surgical tools can be excited by NIR lasers and visualized deep in tissues or blood through a NIR detector or NIR microscope on NIR laparoscopy equipment. A preferred system of the invention includes a laparoscope that includes a light source to stimulate emission from a coated surgical instrument. The light can be coupled into the fiber optical cable of the laparoscope. With a digital detection system, an automated function to detect or help detect a coated object can be implemented via the laparoscope system. This invention provides reliable methods and systems detect objects in patients' bodies, such as retained foreign objects and other medical devices, such as implantable devices or biopsy and surgical markers.

A preferred coating that has been demonstrated experimentally is a coating of polymeric adhesive containing quantum dots or fluorescent and/or NIR dyes on the surface of metal, plastic and other surgical instruments. In experiments, metal surgical instruments were coated. Additional experiments showed the ability to coat on plastic and glass material. Additionally, any surface with reactive hydroxyl groups can be coated. Preferred embodiments including dual coatings, i.e., coatings with two fluorescent and NIR sources selected to respond to different wavelength excitation sources. In a particular preferred embodiment, the two sources respond to UV and NIR light.

Preferred embodiments of the invention will now be discussed with respect to experiments and resultant data. The applications and broader aspects of the invention will be understood by artisans in view of the general knowledge in the art and the description of the experiments that follows.

Figure 1:
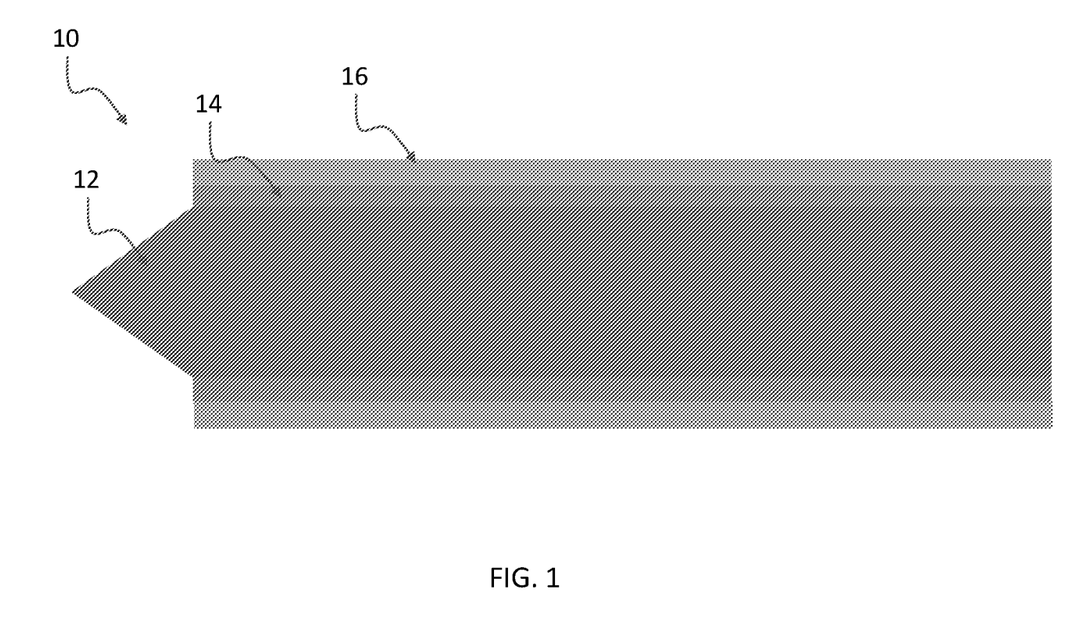
FIG. 1 is a schematic diagram of a preferred embodiment dual fluorescent and NIR (near infrared) coated surgical needle.

FIG. 1 is a schematic representation of a preferred dual coated needle 10. A needle body 12 is metal. The dual coating includes a first layer 14 and a second layer 16, selected to be responsive to emit two different wavelengths. The coatings 14 and 16 each include a quantum dot or a fluorophore. In the experimental embodiment, the first layer 14 included DC fluorescent dye and the second layer 16 included ICG dye. The concentration of ICG in epoxy glue is preferably at least 0.14, more preferably >10 mg/ml, and more preferably 25 mg/ml or higher, up to the solubility limit in the glue mixture or the limit where self-quenching occurs, and the emission intensity begins to decrease as concentration is increased. The concentration of DC dye in the epoxy in experiments was 1.25 mg/g. The minimum concentration produces a detectable response, and the maximum is again the solubility limit, or the limit defined by self-quenching. The NIR excitation can reveal lost foreign objects under up to about 1 cm skin and mesentery but not through organs. Organs have auto-fluorescence and absorb NIR light. A thin layer of liver can block the laser or dye emission, for example. In the experiments, the ICG layer had no effect on the brightness of the underlying DC layer.

Figure 2:
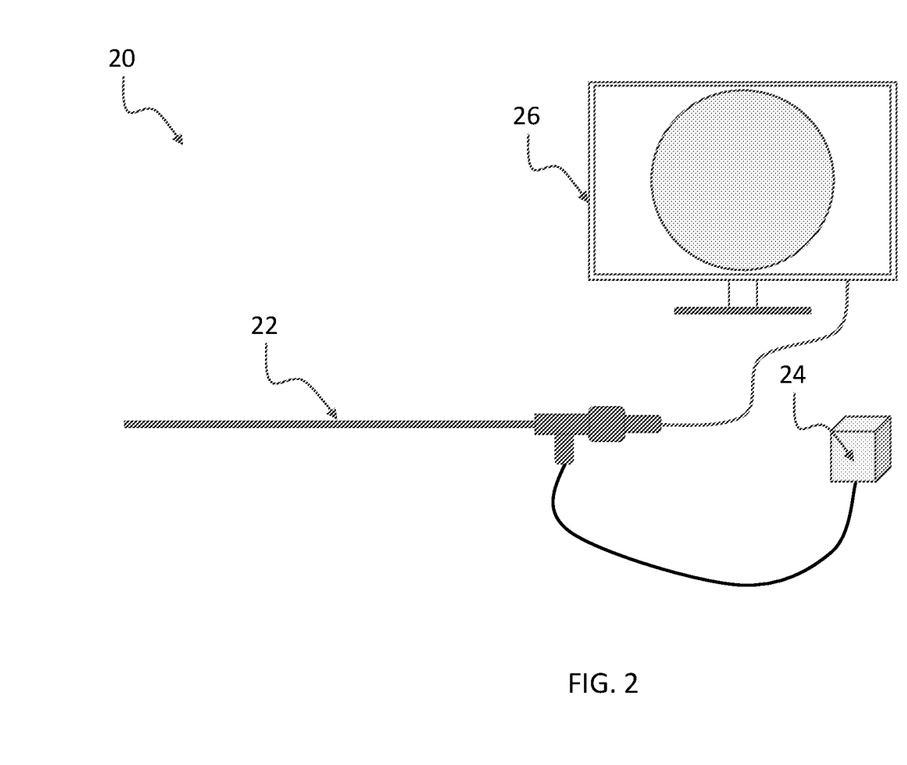
FIG. 2 is a schematic diagram of a preferred embodiment laparosopical surgical system.

FIG. 2 shows a preferred embodiment system laparoscopical surgical system 20 that is used with preferred coated surgical instruments or implants, such as the needle 10 of FIG. 1. A laparoscope 22 receives three separate selectable wavelengths of emission from an emission source 24. The source 24 includes separate white, violet and near infrared wavelength sources that can be selected by a surgeon. The white source is selected to visualize organs and instruments under normal luminary. The violet source is selected to search for coated medical devices by stimulating a fluorescence response. The near IR source is elected to locate coated medical devices via near infrared imaging. A sensor in the laparoscope 22 senses emissions from the distal end of the scope via optical fiber and provides a view from a distal end of the scope 22 via a display 26, which can be part of a computer system that also records, stores and transmits images and/or video.

A preferred coating protocol for the example dual layer DC and ICG embodiment included pretreating the needle with DETA ((N1-(3-Trimethoxysilylpropyl)diethylenetriamine))/methanol solution for 4 hours. Pretreating needles with DETA will covalently bind a monolayer of diethylenetriamine on the surface of metal which can initiate the curing of epoxy resin as hardener and provide a covalent link to the surface. The pretreating enhances epoxy glue adhering to the surface of metal or glass objects that have surface hydroxyl groups. Covalent bonds between the metal surface and glue film can resist the shear force from the clamping and the friction of suturing tools. A DC/methanol solution (5 mg/ml) and an ICG/methanol solution (5 mg/ml) were then prepared. 125 μl of DC/methanol solution, 14 μl of ICG/methanol solution and 111 μl of methanol are combined with 125 mg epoxy glue part B (hardener) were prepared. The mixture is vortexed for 5 minutes before 125 mg of epoxy glue part A (epoxy resin) is added. The mixture is vortexed for an additional minute. Surgical needles are coated with the mixture by dipping the needles into the mixture twice. The coated needles are cured in air for 24 hours at room temperature.

In additional example experimental embodiments with a single layer, InP/ZnS quantum dots with an emission wavelength of 530 nm and 590 nm, rubrene with an emission wavelength of 540 nm and indocyanine green with an emission wavelength of 830 nm were demonstrated as an example fluorescent or NIR emission sources. Methyl 2-cyanoacrylate was demonstrated previously by the present inventors and colleagues as a polymeric adhesive to crosslink silica shells to form a thin 2D film that can be coated on various materials with various thicknesses. See, J. Yang et al, "Ultrasound Responsive Macrophase-Segregated Microcomposite Films for in Vivo Biosensing," ACS Appl. Mater. Interfaces, 9 (2), pp 1719-1727 (2017). The thickness of the thin film containing fluorescent materials can be modified similarly by controlling dip coating parameters and the adhesive viscosity with added solvents. Other types of polymeric matrices can be employed similarly to fabricate thin fluorescent films. Surgical needles coated with the fluorescent films were tested for visibility of fluorescence under surgical conditions.

Experiments have demonstrated QDs/cyanoacrylate film coated needles, which were observed under 12 w black light illumination. The needles coated with 15 μm quantum dot-polymer films emit strong green fluorescence, which can be distinguished easily from the background by human eyes. Different emission wavelengths can be achieved with different quantum dot sizes mixed in the polymer thin film.

A second experimental example was demonstrated through coating of epoxy glue containing InP/ZnS quantum dots on surgical needles, N1-(3-Trimethoxysilylpropyl)diethylenetriamine (DETA) was used to pretreat the needles to enhance the binding between the glue and the needles. Surgical needles were dipped in 1% DETA solution of toluene (v/v) for 4 hours. After pretreating, the needles were rinsed with toluene to remove uncoated DETA. 125 mg of resin and 125 mg of hardener of 2 Ton® Epoxy glue were dissolved in 125 μl of QDs solution of toluene (5 mg/ml), respectively. The two solutions were mixed and the needles were dip-coated in the mixture for 5 times. The glue on the needles was cured at room temperature for 24 hours. Observation of three QDs/glue coated needles before and after passing through chicken meat 30 times showed excellent visibility and that the coating remained intact. Surgical needle drivers and forceps were used to suture the needles. The fluorescence after 30 passes through the chicken meat indicated that the glue coated on needles can resist the friction between the needles and tissues and the repeating clamping of surgical drivers and forceps.

A third experimental example involved the coating of indocyanine green (ICG)/epoxy glue on surgical needles. 125 mg of resin was dissolved in 500 μl of 1 mg/ml ICG solution of methanol, then 125 mg of hardener was added into the solution. Surgical needles were dip-coated 5 times in the solution and cured 24 hours at room temperature. Near field infrared images of ICG/glue coated needles were taken with the excitation of 780 nm. A Fluobeam 800 NIR imaging system were used to excite and image the needles. The needles showed strong NIR emission with the exposure time of 10 ms and 100 ms, respectively, and can be visualized with the exposure time of 1 ms.

A fourth experimental embodiment provided a coating of rubrene/epoxy glue on surgical needles. 125 mg of resin was dissolved in 250 μl of 1 mg/ml rubrene solution of toluene, then 125 mg of hardener was added into the solution.

Surgical needles were dip-coated 5 times in the solution and cured 24 hours at room temperature. The two rubrene/epoxy adhesive coated needles were highly visible under a 12-watt blacklight.

An in vivo test was performance with a New Zealand rabbit. The abdomen of the rabbit was opened, and QDs/cyanoacrylate coated surgical needles were placed randomly under or on the top of the multiple organs such as liver, spleen, stomach and intestines. This was done blind to the second surgeon. After turning off the light in the operation room, the second surgeon located and found the needles under a 12-watt black light, and the duration was recorded. All 8 coated needles hidden were found by the second surgeon. In contrast, only 5 out of 8 of the control needles were found when a second set of 8 coated needles were hidden and the second surgeon did not use the UV light/fluorescence for locating them. Of the 3 needles not found by conventional methods, when using black light, all 3 were then quickly recovered. The average time of locating and finding the coated needles was 42 seconds.

In another in vivo test, the same protocol was deployed with 16 rubrene/epoxy glue coated needles. All 16 needles were recovered under black lights and average time of locating and finding the coated needles was 38 seconds.

Observations of a QDs/cyanoacrylate glue coated needle and a rubrene/epoxy glue coated needle on the top of intestine of a rabbit were made. The strong emission of green fluorescence of the needle can be distinguished from the organ easily by human eyes.

In an example experiment, surgical needles of 11 mm length coated with cyanoacrylate polymer containing either fluorescent QD (n=16) or dyes (n=16) were hidden at random sites within the abdominal cavity of New Zealand rabbits after a standard laparotomy. The surgeon was blinded to the needle location and timed in searching for the control needles (n=16) with standard lighting and the fluorescent needles with a 12 W black light. The surgeon had up to 5 minutes to find the needle; if a control was not found, the surgeon searched for the same needle with black light excitation.

100% of fluorescent QD and dye infused polymer needles were located with significantly less time, average 52 and 38 seconds, respectively, compared to the control needles, 83 seconds ($p<0.05$). Only 75% of the control needles were located within 5 minutes, and all 4 unfound control needles were subsequently identified with the aid of fluorescence within an average of 84 seconds.

The example experimental thin, non-toxic polymer coating of QDs or fluorophores allowed for a significant reduction in the time required for real time needle localization. This technology has the potential to minimize the risk of retained foreign objects by allowing rapid detection of misplaced needles.

| Needle Type | Percent Located Within 300 s | Avg. Time (s) | Avg. Time to Find with Fluorescence (s) | p value |
|---|---|---|---|---|
| Control (n = 16) | 0.75 | 145 | 83 (30, 30, 230, 45) | |
| Fluorescent QD (n = 16) | 1 | 53 | n/a | 0.0119 |
| Fluorescent Dye (n = 16) | 1 | 38 | n/a | 0.0014 |

Dual Coating Experiments

Single coatings can be formed with two emitters (UV and NIR) to provide different responses to be found in open surgery or in laparoscopic procedures. Experiments also demonstrated a two-layer coating. These additional experiments were conducted with dual wavelength coatings that excite under both UV and NIR light, and these coatings were tested on surgical needles. Standard 11 mm (Ethicon) 7-0 reverse cutting needles were coated with the dual layer coating. Epoxy glue was used to apply the dansyl chloride (DC) and indocyanine green (ICG) dyes that were used as fluorescence and NIR labels, respectively, with the metal surface of surgical needles. Methanol was added to dilute the glue and dissolve the dyes. The needles were coated with the mixture by dip coating, and cured in air at room temperature to form a hard polymer-dye film After curing, the content of DC and ICG in the cured glue are 10 mg/g and 0.15 mg/g, respectively. The final coating is clear in color and ranges from 10 to 30 μm thick. During illumination under a black light source with a wavelength of 390 nm, DC emits green fluorescence with a wavelength near 520 nm. ICG dye under illumination with a 980 nm NIR light source will emit NIR light with a wavelength longer than 1000 nm. An additional fluorescent (rubrene) coating was developed to evaluate if the color of the fluorescent needles influences recognition retrieval time in an open setting. Under a black light, rubrene emits orange fluorescence with a wavelength near 560 nm. To enhance the binding of the film with the surface of needle, the needles were pretreated with $N^1$-(3 trimethoxysilylpropyl) diethylenetriamine (DETA) by dipping needles into 1% DETA methanol solution for 4 hours before drying at room temperature overnight. The silane group in DETA reacts with surface hydroxyl groups on the metal, and the amine groups can react with glycidyl groups of the epoxy resin and better anchor the polymer chains to the metal surface.

During the development of the coating, tests to evaluate the adherence of the dye to the needle were performed. Needles were passed through tissue up to 20 times to evaluate for any disruption or flaking of the coating. In addition, the needles were clamped with standard needle holders >30 times to ensure the coating could withstand standard manipulation in an operating room. The coating was also evaluated for any degradation or photo bleaching to ensure that prolonged storage or exposure to intense surgical field lighting would not lead to reduced fluorescence.

After coating the 11 mm needles with the dual DC and ICG dyes, the needles did not have any significant alterations to their appearance or texture. However, the orange fluorescent coating resulted in an orange hue in standard lighting unlike the DC coating. The fluorescent coatings were found to withstand extensive testing including passing the needles through tissue 20 times and repetitive needle manipulation with standard steel needle holders without evidence of flaking or chipping. Dual coated needles in standard light, UV light and with NIR light can be seen after 20 passes through tissue with standard needle holders.

This study was approved by the Institutional Animal Care and Use Committee of the University of California San Diego. In vivo studies were performed to evaluate the utility and efficacy of the fluorescence and ICG coated needles in 10 female New Zealand White rabbits, aged 20-30 weeks. All animals were housed in an approved animal housing facility and kept at 20° C. with a 12 h light/dark cycle and were fed a commercial pelleted diet (Harlan Tecklad) ad libitum. Rabbits were anesthetized with isoflurane gas with oxygen during the open and laparoscopic surgeries. At the conclusion of the experiments, the animals were sacrificed with sodium pentobarbital injection and bilateral thoracotomies. All rabbits were between 3-4 kg at time of operation. Only female rabbits were employed as many of the animals had been initially recruited for an unrelated experiment that mandated all female rabbits.

Search Protocol

To evaluate the effectiveness of the coating in a clinical setting, two separate IACUC approved experiments were completed. To simulate an open laparotomy setting, a standard laparotomy incision from xyphoid to pubis was made and subsequently a total of 52 needles were placed in the abdomen, one at a time, in random locations to which the surgeon was blinded. The location of each needle was recorded, and the surgeon searched for 26 needles with standard light as controls and 26 were searched for with the use of a black light. Time to location of the needle by the surgeon was recorded. To simulate a laparoscopic setting, a standard laparoscopic tower and equipment set was used to establish pneumoperitoneum. A standard 5 mm zero-degree camera was used for access and replaced with a specialized 30-degree FDA approved laparoscope that can detect ICG (indocyanine green) and NIR wavelengths (VisionSense NIR Imaging System, Stryker). A total of 52 needles were searched for in a laparoscopic setting, 26 with a standard camera (control) and 26 with an ICG capable laparoscope. Maximum time allotted for location of all needles, in both open and MIS procedures, was 300 s. If at 300 s the surgeon had not found the needle, the search was repeated with black light or ICG fluoroscope, as appropriate. The open protocol was also repeated with the orange fluorescent, rubrene-coated needles to assess for time variance secondary to color.

Mann Whitney non-parametric tests were employed to compare the time to location of fluorescent and ICG coated needles against their respective controls at a P value of 0.05. Statistics were calculated in IBM SPSS Statistics for Macintosh, Version 22.0. and figures were created in GraphPad Prism 7.

On average, the surgeon required 149.3±46.7 seconds to locate twenty-six 11 mm dual coated control needles in normal lighting. A total of 9 control needles (34.6%) could not be located within the maximum allotted 300 s. All 9 of the lost control needles were then located with the use of the UV light and fluorescent coating within 300 s (mean 51.89, range 2-70 s). All the coated needles searched for under black light were found within 300 s (mean time 53.5±46.7 s). The time to locate the needles with the use of the fluorescent coating was significantly less than the time to locate the needles in the control setting, P=0.0027. The time to locate the needles with the aid of green fluorescence was reduced by 64% with an overall 100% success rate.

A separate experiment was completed utilizing the orange fluorescent coating on 26 of the same 11 mm sized needles. On average the surgeon took 43.26±59.93 s to locate the orange fluorescent needle under black light illumination. One needle could not be found within the allotted time with this coating (3.8%). No significant difference was found between the time to location of the dual coated green fluorescent needles and the orange fluorescent needles (P=0.1786). Relative to control settings, the fluorescent orange coating significantly reduced the time to retrieval of the needle (P<0.0001).

In the laparoscopic setting, the surgeon required on average 164.7±116.5 s to locate the needles with a standard laparoscope. A total of 9 of the control needles could not be located within 300 s, and 88.9% (n=8) of these 9 could be located with the ICG capable laparoscope within an average of 75.33±90.47 s (range 2-90 s). All the needles initially searched for with the ICG laparoscope were located within 300 s in an average of 43.92±28.93 s. The needles searched for with dual coating were found significantly faster and more frequently than the control needles (P<0.0001). Overall, while the dual coating significantly improved the frequency of locating the needle in both settings, the ICG coating was found to have a more significant reduction in time to retrieve the needle. Altogether, the time to locate the coated needles with the aid of ICG was reduced by 74% with an overall 100% success rate.

| | Percent Not Located Within 300 s* | Max Time (s) | Mean Time (s) | Mean Time to Locate Lost Control Needles (s) | Total Time Searched (minutes, % control) | P Value (compared to control) |
|---|---|---|---|---|---|---|
| Open Surgery | | | | | | |
| Control (n = 26) | 35% | 300* | 149 ± 116 | 51 ± 67 (n = 9) | 64.68 (100%) | — |
| Black Light Assisted (green) (n = 26) | 0% | 165 | 53 ± 47 | n/a | 23.18 (36%) | 0.0027 |
| Black Light Assisted (orange) (n = 26) | 4% | 300* | 43 ± 60 | n/a | 18.75 (28%) | <0.0001 |
| Laparoscopic | | | | | | |
| Control (n = 26) | 35% | 300* | 164 ± 116 | 75 ± 90 † (n = 9) | 71.38 (100%) | — |
| ICG assisted (n = 26) | 0% | 118 | 44 ± 29 | n/a | 19.03 (26%) | <0.0001 |

The invention claimed is:

1. A composition for coating a medical device, the composition comprising a polymeric matrix comprising two different wavelength emitting non-toxic quantum dots, and/or a fluorophores, wherein the polymeric matrix contains the quantum dots and/or fluorophores and binds as a coating to the medical device, and the non-toxic quantum dots and/or fluorophores are selected to provide response in both of a visible and near infrared (NIR) light range to be located using human vision in response to stimulation by a low-power ultraviolet black light source with an excitation wavelength between 320 nm to 400 nm and with a detector in response to an NIR excitation source, wherein the polymeric matrix is selected from the group consisting of epoxy adhesive, cyanoacrylate glue, polymeric organosilicon, and polymeric gels.

2. A composition for coating a medical device, the composition comprising a polymeric matrix comprising two different wavelength emitting non-toxic quantum dots, and/or a fluorophores, wherein the polymeric matrix contains the quantum dots and/or fluorophores and binds as a coating to the medical device, and the non-toxic quantum dots and/or fluorophores are selected to provide response in both of a visible and near infrared (NIR) light range to be located using human vision in response to stimulation by a low-power ultraviolet black light source with an excitation wavelength between 320 nm to 400 nm and with a detector in response to an NIR excitation source, wherein the quantum dots are selected from the group consisting of III-V group compounds, I-III-VI2 group compounds, and ZnS/ZnSe nanocrystals.

3. The composition of claim 2, wherein the fluorophore is selected from the group consisting of inorganic fluorescent dyes, organic fluorescent dyes, luminescent metal doped alumina, rubrene, rhodamine, indocyanine green, and dansyl chloride.

4. The composition of claim 3, wherein the fluorophore comprises indocyanine green.

5. The composition of claim 3, wherein the fluorophore is indocyanine green and the polymer matrix is epoxy glue in a fluorescent dye to polymer ratio of at least 0.14 mg/ml.

6. The composition of claim 5, wherein the fluorescent dye to polymer ratio is >10 mg/ml.

7. The composition of claim 2, wherein the fluorescent dye to polymer ratio is set below a limit where significant self-quenching occurs.

8. A composition for coating a medical device, the composition comprising a polymeric matrix comprising two different wavelength emitting non-toxic quantum dots, and/or a fluorophores, wherein the polymeric matrix contains the quantum dots and/or fluorophores and binds as a coating to the medical device, and the non-toxic quantum dots and/or fluorophores are selected to provide response in both of a visible and near infrared (NIR) light range to be located using human vision in response to stimulation by a low-power ultraviolet black light source with an excitation wavelength between 320 nm to 400 nm and with a detector in response to an NIR excitation source, wherein the fluorophore comprises dansyl chloride.

9. A composition for coating a medical device, the composition comprising a polymeric matrix comprising two different wavelength emitting non-toxic quantum dots, and/or a fluorophores, wherein the polymeric matrix contains the quantum dots and/or fluorophores and binds as a coating to the medical device, and the non-toxic quantum dots and/or fluorophores are selected to provide response in both of a visible and near infrared (NIR) light range to be located using human vision in response to stimulation by a low-power ultraviolet black light source with an excitation wavelength between 320 nm to 400 nm and with a detector in response to an NIR excitation source, wherein the polymer matrix comprises epoxy glue or cyanoacrylate glue.

10. A composition for coating a medical device, the composition comprising a polymeric matrix comprising two different wavelength emitting non-toxic quantum dots, and/or a fluorophores, wherein the polymeric matrix contains the quantum dots and/or fluorophores and binds as a coating to the medical device, and the non-toxic quantum dots and/or fluorophores are selected to provide response in both of a visible and near infrared (NIR) light range to be located using human vision in response to stimulation by a low-power ultraviolet black light source with an excitation wavelength between 320 nm to 400 nm and with a detector in response to an NIR excitation source, having one of InP/ZnS quantum dots and rubrene for the response in the visible light range and indocyanine green for the response in the NIR light range, and the polymer matrix consists of one of methyl 2-cyanoacrylate, polymeric organosilicon and epoxy glue.

11. A medical device coated with a coating approximately 5 μm to 20 μm in thickness, wherein the coating is a composition comprising a polymeric matrix comprising two different wavelength emitting non-toxic quantum dots, and/or a fluorophores, wherein the polymeric matrix contains the quantum dots and/or fluorophores and binds as a coating to the medical device, and the non-toxic quantum dots and/or fluorophores are selected to provide response in both of a visible and near infrared (NIR) light range to be located using human vision in response to stimulation by a low-power ultraviolet black light source with an excitation wavelength between 320 nm to 400 nm and with a detector in response to an NIR excitation source.

12. The medical device of claim 11, wherein the medical device comprises a metal or plastic surface and the coating is applied to said metal or plastic surface.

13. The medical device of claim 11, wherein the medical device is a surgical needle.

14. The medical device of claim 11, wherein the medical device is selected from the group consisting surgical needles, forceps, razor blades, medical implants, image guided injection needles, and biopsy markers.

15. A method for locating a medical device, the method comprises providing one or more medical devices according to claim 14 and stimulating emission from the coating with one or both of a low-power ultraviolet black light source and the NIR excitation source and detecting emissions in one or both of the visible and near infrared (NIR) light range to locate the medical device.

16. A surgical system, comprising a low-power ultraviolet black light source with an excitation wavelength between 320 nm to 400 nm or an NIR excitation source and a medical device according to claim 14.

17. The system of claim 16, wherein the excitation source comprises a laparoscope, wherein the laparoscope includes selectable white, violet and near infrared sources and is configured to a selected source through an optical fiber to a surgical site and includes a sensor for detecting emissions of the quantum dots and the fluorescent dye.

18. A method for coating a surgical needle, the method comprising mixing two different wavelength emitting fluorescent quantum dots and/or fluorophores with a polymer to create a coating solution, wherein the non-toxic quantum dots and/or fluorophores are selected to provide response in both of a visible and near infrared (NIR) light range to be located using human vision in response to stimulation by a low-power ultraviolet black light source with an excitation wavelength between 320 nm to 400 nm and with a detector in response to an NIR excitation source;

pretreating the surgical needle with N1-(3 trimethoxysilylpropyl) diethylenetriamine (DETA) by dipping the surgical needle into a DETA methanol solution for a predetermined period following by drying at room temperature to covalently bind a monolayer of diethylenetriamine on the metal surface;

dip coating the surgical needle in the coating solution; and curing the coating on the surgical needle.

* * * * *